Figure 1:
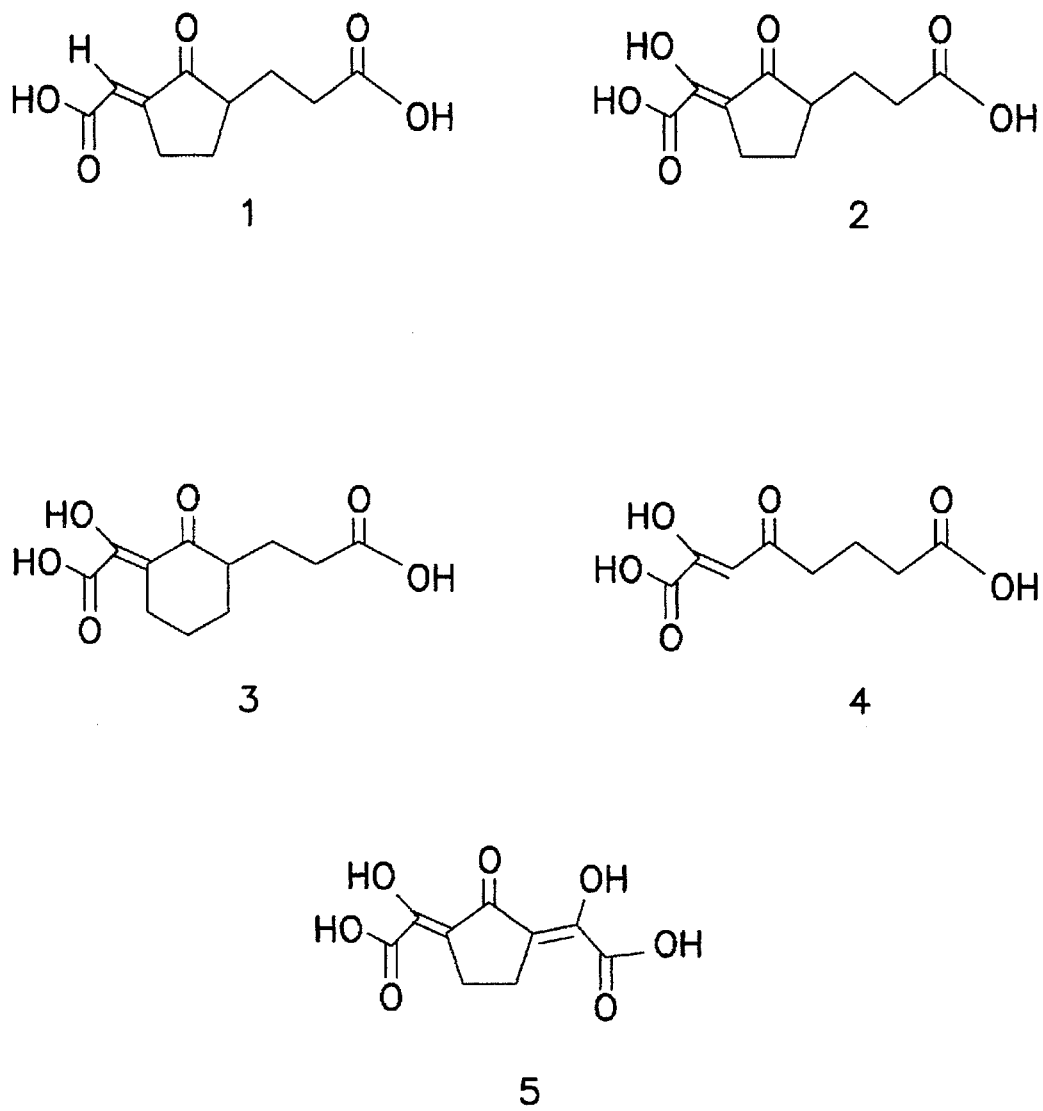

United States Patent [19]

Kraus et al.

[11] Patent Number: 5,648,318

[45] Date of Patent: Jul. 15, 1997

[54] KETODIACID COMPOUNDS THAT INHIBIT NEMATODE EGG HATCHING

[75] Inventors: George A. Kraus; Gregory L. Tylka, both of Ames, Iowa

[73] Assignee: Iowa State University Research Foundation, Ames, Iowa

[21] Appl. No.: 387,108

[22] Filed: Feb. 10, 1995

[51] Int. Cl.$^6$ .................................................. A01N 31/00
[52] U.S. Cl. .................................................. 504/320
[58] Field of Search .................................................. 504/320

[56] References Cited

PUBLICATIONS

*Biology and Management of the Soybean Cyst Nematode*, R.D. Riggs et al., Eds.; APS Press: St. Paul, MN (1992)—(title page, copyright page and Table of Contents only).

E.J. Corey et al., "Total Synthesis of Glycinoeclepin A", *J. Am. Chem. Soc.*, 112, 8997–8998 (1990).

B. Doupnik, Jr., "Soybean Production and Disease Loss Estimates for North Central United States From 1989 to 1991", *Plant Disease*, 77, 1170–1171 (Nov. 1993).

G.A. Kraus et al., "Synthesis and Evaluation of Compounds that Affect Soybean Cyst Nematode Egg Hatch", *J. Agric. Food Chem.*, 42, 1839–1840 (1994).

T. Masamune et al., "Isolation of a natural hatching stimulus, glycinoeclepin A, for the soybean cyst nematode", *Nature*, 297, 495–496 (Jun. 10, 1982).

T. Masamune et al., "Glycinoeclepins, Natural Hatching Stimuli for the Soybean Cyst Nematode, Heterodera Glycines. I. Isolation", *Bull. Chem. Soc. Jpn.*, 60, 981–999 (1987).

A. Miwa et al., "Synthetic Study on Hatching Stimuli for the Soybean Cyst Nematode", *Agric. Biol. Chem.*, 51, 3459–3461 (1987).

K. Mori et al., "Recent results in the synthesis of semiochemicals: synthesis of glycinoeclepin A", *Pure & Appl. Chem.*, 61, 543–546 (1989).

A. Murai et al., "Total Synthesis of Glycinoeclepin A", *J. Am. Chem. Soc.*, 110, 1985–1986 (1988).

T.L. Niblack et al., "Soybean Yield Losses Due to *Heterodera glycines* in Iowa", *Plant Disease*, 76, 943–948 (Sep. 1992).

"Protect Your Soybean Profits: Manage Soybean Cyst Nematode"; T.L. Niblack, Ed.; United Soybean Board (Aug. 1993).

G. Sciumbato, "Soybean Disease Loss Estimates for the Southern United States During 1988–1991", *Plant Disease*, 77, 954–956 (Sep. 1993).

(List continued on next page.)

*Primary Examiner*—Deborah D. Carr
*Attorney, Agent, or Firm*—Schwegman, Lundberg, Woessner & Kluth, P.A.

[57] ABSTRACT

A method for inhibiting hatching of soybean cyst nematode eggs is provided comprising contacting said eggs with an effective inhibitory amount of a compound of formula (I):

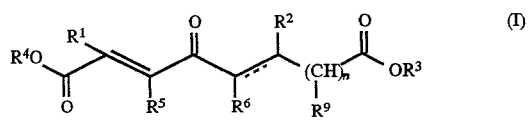

wherein $R^1$ is H or OH, $R^2$ is H or OH, $R^3$ is H or $(C_1-C_4)$alkyl, $R^4$ is H or $(C_1-C_4)$alkyl, $R^5$ and $R^6$ are individually H, $(C_1-C_5)$alkyl, $C_3-C_6$(cycloalkyl)alkyl, $C_5-C_7$(cycloalkenyl)alkyl, $(C_6-C_{12})$aryl, $(C_7-C_{12})$aralkyl, trans$(C_4-C_5)$alkenyl, allyl or furan-2-ylalkyl or together are $(C_2-C_5)$alkylene, or $(C_3-C_5)$alkylidene or 1,2-phenylene, optionally substituted by OH, O$(C_1-C_3)$alkyl, SH, phenyl or N$(R^7)(R^8)$, wherein $R^7$ and $R^8$ are individually H, $(C_1-C_3)$ alkyl or phenyl; $R^9$=H or $(C_1-C_4)$alkyl, n is 0 or 1 and wherein the bond represented by --- is present when n=0 or absent when n=1; or an agronomically-acceptable salt thereof.

18 Claims, 1 Drawing Sheet

1

2

3

4

5

OTHER PUBLICATIONS

G. Tylka, *Soybean Cyst Nematode,* Iowa State University Cooperative Extension Service, Publication PM-879 (1994).

H. Watanabe et al., "Triterpenoid Total Synthesis. Part 2. Synthesis of Glycinoeclepin A, a Potent Hatching Stimulus for the Soybean Cyst Nematode", *J. Chem. Soc. Perkin Trans.,* 1, 2919–2934 (1991).

A.T.S. Wong et al., "Effects of Eight Herbicides on In Vitro Hatching of *Heterodera glycines*", *Journal of Nematology,* 25, 578–584 (Dec. 1993).

KETODIACID COMPOUNDS THAT INHIBIT NEMATODE EGG HATCHING

BACKGROUND OF THE INVENTION

Cyst nematodes are serious pests of many crops, and their extermination or control is an important agricultural problem. For example, soybean cyst nematode (SCN) is currently the most prevalent and consistently occurring pest of soybeans in the midwestern United States. At present, SCN is known to infest 64 of 99 Iowa counties and is suspected to be present in an additional 10 to 20 counties. Infestation causes dwarfing or stunting of roots, and stunting and yellowing of foliage. Soybean yield losses due to SCN can be as great as 50 to 75% when SCN densities are high or under drought conditions as occurred in parts of Iowa in 1988 through 1990. Current SCN management options include use of SCN-resistant soybean varieties and rotation with nonhost crops such as corn. See, G. L. Tylka et al., Soybean Cyst Nematode, Iowa State University Cooperative Extension Service, Publication PM-879 (1994).

A four-year rotation of nonhost, SCN-resistant soybean, nonhost, SCN-susceptible soybean is recommended to growers for fields with low SCN densities. Alternating use of SCN-resistant and SCN-susceptible soybeans is necessary to maintain the effectiveness of the soybean resistance. If SCN resistance is used continuously, the nematode adapts to the resistance and a race shift occurs. The aforementioned rotation can be effective at keeping low SCN densities from increasing, but is not very effective at reducing existing high densities of SCN. Unfortunately, many growers discover SCN infestations only after nematode densities have reached moderate to high densities. In such instances, growers are recommended to plant successive years of corn or some other SCN nonhost. However, growers often are unable to plant corn in the same field for several years in a row because of the limited corn acreage allowed by federal government programs, and there is not an economically viable third crop available for most growers in the upper Midwest.

In the early 1980s, T. Masamune et al., Nature, 297, 495 (1982), reported the extraction of a terpenoid called glycinoeclepin A from the roots of kidney bean plants and found that it stimulated hatch of SCN eggs at very low concentrations. The structure of this compound is shown below:

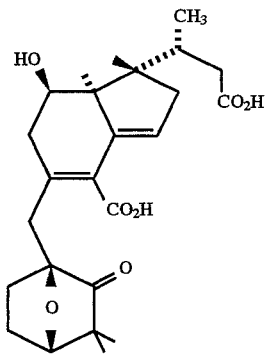

Glycinoeclepin A can potentially be used to decrease SCN densities in infested soil if applied to fields during years when a nonhost crop, such as corn, is planted. SCN is an obligate parasite that must infect host soybean roots to live and multiply. SCN eggs "tricked" into hatching in the absence of a host soybean crop will die within days or weeks due to starvation, parasitism, or predation. Unfortunately, glycinoeclepin A is present in such small amounts in kidney bean roots that extraction of large quantities sufficient for application to agricultural fields is not possible. Since glycinoeclepin A was first identified, several research groups have successfully synthesized the compound or subunits thereof. For example, see E. J. Corey et al., J. Amer. Chem. Soc., 112, 8997 (1990); A. Miwa et al., Agricultural Biol. Chem., 51, 3459 (1987); K. Mori et al., Pure Appl. Chem., 61, 543 (1989) and G. A. Kraus et al., Agricultural Food Chem., 42, 1839 (1994). However, all of the prior synthetic routes are very complicated and, consequently, time-consuming and expensive to perform. Furthermore, these published synthetic routes result in the production of only micrograms or milligrams of the target compound. For practical agricultural application purposes, hundreds to thousands of grams of glycinoeclepin A will be needed. Therefore, them is a continuing need for compounds that can be used to control the timing of cyst nematode egg hatch.

SUMMARY OF THE INVENTION

The present invention provides compounds useful to inhibit (delay or prevent) the hatching of soybean cyst nematode (SCN, Heterodera glycines) eggs, and methods of using the compounds for this purpose, comprising contacting soybean cyst nematode eggs with an effective inhibitory amount of a compound of formula (I):

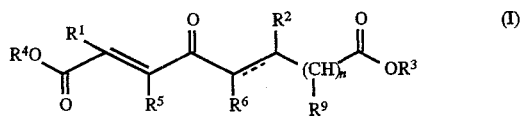

wherein $R^1$ is H or OH, $R^2$ is H or OH, $R^3$ is H or $(C_1-C_4)$alkyl, $R^4$ is H or $(C_1-C_4)$alkyl, $R^5$ and $R^6$ are individually H, $(C_1-C_5)$alkyl, $C_3-C_6$(cycloalkyl)alkyl, $C_5-C_7$(cycloalkenyl)alkyl, $(C_6-C_{12})$aryl, $(C_7-C_{12})$aralkyl, trans$(C_4-C_5)$alkenyl, allyl furan-2-ylalkyl or together are $(C_2-C_5)$alkylene, $(C_3-C_5)$alkylidene or 1,2-phenylene, optionally substituted by OH, $O(C_1-C_3)$alkyl, SH, phenyl or $N(R^7)(R^8)$, wherein $R^7$ and $R^8$ are individually H, $(C_1-C_3)$ alkyl or phenyl; $R^9$ is H or $(C_1-C_4)$alkyl, n is 0 or 1, wherein the bond represented by --- is present when n=0 or absent when n=1; or an agronomically acceptable salt thereof.

Preferably, $R^3$ and $R^4$ are H, $R^5$ and $R^6$ are both H, $CH_3$, or together, are ethylene (—$(CH_2)_2$—), propylene (—$(CH_2)_3$—) or butylene (—$(CH_2)_4$—), $R^9$ is H, n=1 and/or the bond represented by --- is absent, i.e., the carbon bonded to $R^2$ is quaternary (—$CH(R_2)$—).

One or more of the compounds of formula (I) can be applied to the soil, having nematode eggs therein, in pure form, i.e., as a dust, but preferably, the compound or a mixture thereof is applied to the target soil in combination with an agronomically-acceptable carrier. Such carriers include solid carriers, liquid carriers, or mixtures thereof, such as a dispersion of a particulate inert solid having a compound of formula (I) absorbed thereon, in a non-phytotoxic liquid carrier, such as water, or an aqueous-alcohol blend. Dispersion or solution of the present compounds in liquid carriers can be assisted by a minor but effective amount of a surfactant, which also assists in wetting the target soil and the eggs therein.

The compounds of formula (I), although sharing some structural features with glycinoeclepin A, were unexpectedly found to inhibit, or delay, the hatching of soybean cyst nematode eggs, rather than to stimulate, or accelerate the egg hatching. Of course, application of an amount of the compound effective to block egg hatching would prevent crop infection, but delaying the egg hatching is also a useful pest control tool, since the host plants, i.e., the soybean plants can become established to the extent that they are not significantly damaged by parasite infection.

Thus, the present compounds can be used to protect the crop species that are hosts for soybean cyst nematodes, including soybean, kidney bean and adzuki bean. However, it is also expected that the compounds of formula I will be effective to inhibit or accelerate the hatching of the eggs of other cyst nematodes, including those of the genus Globodera, and other plant parasitic nematode species, i.e., Meloidogyne (root knot nematodes).

BRIEF DESCRIPTION OF THE DRAWING

FIG. 1 depicts the structures of several preferred embodiments of formula (I): 2-(2'-carboxyethyl)-5-(carboxymethylidenyl)cyclopentanone (1); 2-(2'-carboxyethyl)-5-[carboxy(hydroxy)methylidenyl] cyclopentanone (2); 2-(2'-carboxyethyl)-6-[carboxy (hydroxy)methylidenyl]cyclohexanone (3); 2-hydroxy-4-oxo-2-octendioic acid (4); and 2-[carboxy(hydroxy) methylidenyl]-5-[carboxy(hydroxy)methylidenyl] cyclopentanone (5).

DETAILED DESCRIPTION OF THE INVENTION

Compounds of formula I wherein the bond represented by --- is present and n=0 can be prepared from ketones of formula $R^5$—$CH_2$—C(O)—$CH_2$—$R^6$ by sequential reaction with diethyloxalate in the presence of alkoxide to yield bis(ketoesters) of the formula $R^5$—$CH(CO_2CO_2Et)C(O)CH(COCO_2Et)$—$R^6$. Reaction of the bis(ketoester) with an alkali metal hydroxide, such as LiOH, in alcohol, affords compounds of formula I, wherein the bond represented by --- is present, n=0, and $R^3$ and $R^4$ are one equivalent of a metal cation.

Compounds of formula I wherein the bond represented by --- is absent and n=1 can be prepared from ketones of formula $R^5$—$CH_2$—C(O)—$CH_2$—$R^6$, by first activating one alpha-carbon via condensation with an acidic amine to yield a compound of the formula (II): $R^5$—$CH_2$—C(P)=CH—$R^6$, wherein P is the residue of an acidic amine such as pyrrolidone. Compound II is then condensed with a compound of the general formula $R^2$—CH═$CR^9$—$CO_2X$ wherein X is a $(C_1$–$C_4)$alkyl group to yield a compound of the formula $R^5$—$CH_2$—C(O)—$CHR^6$—$CHR^2$—$CH(R^9)CO_2X$. Further reaction of this compound with diethyloxalate, followed by reaction of the ketoester with hydroxide, yields a compound of the formula (I) wherein the bond represented by --- is absent and n=1.

The invention also comprises the agronomically acceptable salts of the biologically active compounds of formula I, preferably in combination with a agronomically acceptable carrier for administration in effective, non-toxic form to the target plot of soil. Agronomically-acceptable salts and carriers are selected so that the finished formulations have no deleterious effects on beneficial soil organisms, the target plants, animals or human handlers.

Pharmaceutically acceptable amine salts may be salts of organic acids, such as acetic, citric, lactic, malic, tartaric, p-toluene sulfonic acid, methane sulfonic acid, and the like as well as salts of pharmaceutically acceptable mineral acids such as phosphoric, hydrochloric or sulfuric acid, and the like. Physiologically acceptable carboxylic acid salts include alkali metal carboxylates and quaternary ammonium salts. These physiologically acceptable salts are prepared by methods known in the art, e.g., by dissolving the free amine bases with an excess of the acid in aqueous alcohol, or neutralizing a free carboxylic acid with an alkali metal base such as a hydroxide; or with an amine.

The present compounds can be applied singly or in admixture for control of SCN. The compounds can be applied in their pure form, as crude mixtures, or as agronomic formations. Such formulations are characterized by the presence of adjuvants that promote effective use of the active compounds and contribute toward economical practice of the invention. In some situations a solvent might be desirable, in other instances a bodying material such as a pulverulent solid might be desirable. Liquids and solids which are used to dilute the active compounds are termed carriers. In still other situations, wetting or dispersing agents, or even other active ingredients might be desired.

Agronomic formulations include, for example, solutions, liquid suspensions, emulsions, wettable powders, dusts, emulsifiable concentrates, and granular formulations. In general, the active component is present in a dispersed or readily dispersible form. Dispersibility promotes thorough and uniform coverage of, or contact with, any target plot of soil, so that the desired control of SCN is realized. When selective SCN control in a crop area or turf is desired, a non-phytotoxic carrier is preferred. In this way, the crop plants or desirable grasses are not injured, but the SCN egg hatch is selectively inhibited. Water is a common non-phytotoxic carrier. Solids ordinarily employed in herbicidal formulations are organic (plant) inorganic (mineral) materials which are not phytotoxic.

The efficacy of the present compounds against SCN eggs is high, and the compounds can be applied at relatively low rates per acre for controlling SCN. For example, useful concentrations in the field can be extrapolated based on known SCN egg densities, based on the working examples below. It will be understood, of course, that a choice of concentration of active ingredient depends upon the method of application as well as the type of formulation and the degree of nematocidal control desired.

The granular formulations of this invention are prepared with about 0.25% to about 75%, preferably 0.50% to 25% by weight, of active ingredient and a granular carrier, for example, heat expanded vermiculite, heat expanded perlite, pyrophyllite, or attapulgite. The active ingredient can be dissolved in a volatile solvent such as methylene chloride, acetone, and the like, and sprayed on the granular carrier as it is stirred or tumbled. The granules are then dried. The granular carrier can range in particle size from about 10 to about 60 mesh, preferably about 30 to 60 mesh.

The dust compositions of the invention are prepared by intimate admixture of from about 0.25% to about 80% by weight, preferably 0.50% to 20% of the active ingredient with a solid pulverulent carrier such as a clay, silica, diatomaceous earth, gypsum and the like, which maintains the composition in a dry, free-flowing condition. The dusts of the invention can be prepared by admixing the compound with the solid diluent and then milling. Preferably, however, the active ingredient is dissolved in a volatile organic solvent, of the kinds indicated above, and then sprayed on the solid carrier so as to assure thorough distribution. The mixture is then dried and milled to the desired size, e.g., less than about 60 microns. A useful composition, in accordance with the invention, is a dispersible powder which is prepared by incorporating a surfactant in a dust composition prepared as described above. Such a dispersible powder can be suspended in water to a desired concentration and applied to soil by conventional spray equipment. Conveniently the dispersible powders are formulated with higher concentrations of active ingredient than the dust compositions, for example, up to about 90%, preferably about 10% to 20%. Surfactants useful in preparing such dispersible powder compositions include anionic and nonionic surfactants, including those described in Waiters (U.S. Pat. No. 5,310,771).

The compounds of this invention can be applied to soil in aqueous sprays without a solid carrier. However, since the compounds themselves are relatively insoluble in water they are preferably dissolved in a suitable inert organic solvent carrier. If the solvent carrier is immiscible with water, an emulsion of the solvent carrier in water can be prepared. If, for example, a water-miscible solvent carrier such as acetone or ethanol is used, the solvent carrier will dissolve in the water and any excess compound (I) will not dissolve. In an emulsion, the solvent phase is dispersed in the water phase and the active ingredient is held in solution in the dispersed phase.

The emulsifiable concentrates of the invention are prepared by dissolving the active ingredient and a surfactant in a substantially water-immiscible solvent carrier (i.e., a solvent carrier which is soluble in water to the extent of less than 2.5% by volume at temperatures of the order of 20° to 30° C.), for example, cyclohexanone, methyl propyl ketone, summer oils, ethylene dichloride, aromatic hydrocarbons such as toluene, and xylene, and high-boiling petroleum hydrocarbons such as heavy aromatic naphtha kerosene, diesel oil, and the like. If desired, a cosolvent such as methyl ethyl ketone, acetone, and the like can be included with the solvent carrier in order to enhance the solubility of the active ingredient. Aqueous emulsions are then prepared by mixing with water to give any desired concentration of active ingredient.

The concentration of active ingredient in the dispersible powder and emulsifiable concentrates from which the aqueous spray formulations are prepared can be as high as 99.5% by weight. The concentration of active ingredient in the dust and granular formulations of the invention can vary from about 0.25% to about 75% or more, but preferably is about 0.50% to 25%.

The formulations containing the active compounds can be applied to soil or to plant growth media, e.g., turf, by conventional methods. For example, an area of soil can be treated prior to or after seeding by spraying wettable powder suspensions, emulsions or solutions from boom-type power sprayers or from hand-operated knapsack sprayers. The formulation can be mixed with subsurface soil by injection or cultivation.

The invention will be further described by reference to the following detailed examples, wherein all starting materials used were of reagent purity and used as supplied. THF was dried over sodium and benzophenone. $^1$H NMR data was obtained on a 300 MHz Nicollet spectrometer and CDCl$_3$ was used as the solvent. All purification was performed by flash chromatography using silica gel and n-hexane/ethyl acetate as eluent.

EXAMPLE 1

2-(2'-Carboxyethyl)-5-[carboxy(hydroxy) methylidenyl]cyclopentanone (2)

To a stirred solution of 1-pyrrolidino-1-cyclopentene (0.300 g, 2.2 mmol) in 5 mL dry dioxane was added 0.291 g (3.4 mmol, 1.55 equiv.) of methyl acrylate. After refluxing for 48 hours, the reaction mixture was quenched with 10 mL of water and refluxed for an additional 8 hours. The resulting mixture was cooled to room temperature and extracted with 1:1 diethyl ether/1$\underline{M}$ HCl. The combined organic layers were dried over Na$_2$SO$_4$ and concentrated on a rotary evaporator. Flash chromatography on silica gel, eluting with n-hexane/ethyl acetate (4:1) gave 0.323 g (87%) of the keto-ester as a pale yellow viscous liquid.

The above keto-ester (0.300 g, 1.76 mmol) was combined with 0.282 g (1.94 mmol, 1.1 equiv.) of diethyl oxalate and cooled to 0° C. In a separate flask, 0.299 g (2.46 mmol, 1.4 equiv.) of potassium t-butoxide was suspended in 3.5 mL dry THF and cooled to 0° C. The keto-ester/diethyl oxalate mixture was added dropwise over 1 hour via syringe pump to the stirring THF solution at 0° C. The reaction was allowed to stir overnight and then acidified with 6$\underline{M}$ HCl to pH=2. The solution was diluted with 3.5 mL of water and extracted 3× with CH$_2$Cl$_2$. The combined organic layers were dried over Na$_2$SO$_4$ and concentrated on a rotary evaporator. Flash chromatography on silica gel, eluting with n-hexane/ethyl acetate (4:1) gave 0.430 g (86%) of the bis-ethyl ester.

The bis-ethyl ester (0.300 g, 1.25 mmol) was dissolved in 2.5 mL of methanol. To this solution 0.240 g (10 mmol, 8 equiv.) of lithium hydroxide and 0.280 g (5 mmol, 4 equiv.) of potassium hydroxide were added. The mixture stirred for 48 hrs and was acidified with 6$\underline{M}$ HCl to pH=2. The mixture was diluted with 2.5 mL water and extracted 3× with CH$_2$Cl$_2$. The combined organic layers were dried over Na$_2$SO$_4$ and concentrated on a rotary evaporator. The crude product was again dissolved in CH$_2$Cl$_2$ and made basic to pH=11 with 15% NaOH. The mixture was washed 3× with diethyl ether, reacidified to pH=2 with 6$\underline{M}$ HCl, extracted 3× with CH$_2$Cl$_2$, dried over Na$_2$SO$_4$ and concentrated on a rotary evaporator yielding the pure title compound (0.251 g, 95%). 300 MHz $^1$H NMR (CDCl$_3$) δ 2.52–2.47 (t, 1H), 2.38–2.00 (m, 4H), 1.84–1.50 (m, 4H). IR (neat) vmax 3100 (m), 2961 (m), 2876 (m), 1735 (s), 1714 (s), 1454 (s), 1408 (m), 1295 (w), 1201 (m), 1160 (m), 933 (w), 917 (w).

EXAMPLE 2

2'(2'-carboxyethyl)-5-(carboxymethylidenyl) cyclopentanone (1)

To a stirred solution of 1-pyrrolidino-1-cyclopentene (0.300 g, 2.2 mmol) in 5 mL dry dioxane was added 0.291 g (3.4 mmol, 1.55 equiv.) of methyl acrylate. After refluxing for 48 hours, the reaction mixture was quenched with 10 mL of water and refluxed for an additional 8 hours. The resulting mixture was cooled to room temperature and extracted with 1:1 diethyl ether/1 $\underline{M}$ HCl. The combined organic layers were dried over Na$_2$SO$_4$ and concentrated on a rotary evaporator. Flash chromatography on silica gel, eluting with n-hexane/ethyl acetate (4:1) gave 0.323 g (87%) of the keto-ester as a pale yellow viscous liquid.

The above keto-ester (0.300 g, 1.76 mmol) was combined with 0.282 g (1.94 mmol, 1.1 equiv.) of diethyl oxalate and cooled to 0° C. In a separate flask, 0.299 g (2.46 mmol, 1.4 equiv.) of potassium t-butoxide was suspended in 3.5 mL dry THF and cooled to 0° C. The keto-ester/diethyl oxalate mixture was added dropwise over 1 hour via syringe pump to the stirring THF solution at 0° C. The reaction was allowed to stir overnight and then acidified with 6$\underline{M}$ HCl to pH=2. The solution was diluted with 3.5 mL of water and extracted 3× with CH$_2$Cl$_2$. The combined organic layers were dried over Na$_2$SO$_4$ and concentrated on a rotary evaporator. Flash chromatography on silica gel, eluting with n-hexane/ethyl acetate (4:1) gave 0.430 g (86%) of the bis-ethyl ester.

To a solution of 0.231 g (2.5 mmol, 2.5 equiv.) glyoxalic acid monohydrate in 3.5 mL of 0.5$\underline{M}$ Na$_2$HPO$_4$ and 1.5 mL of 1$\underline{M}$ KH$_2$PO$_4$ cooled to 0° C., 0.300 g (1.05 mmol 1 equiv.) of the bis-ethyl ester was added dropwise along with an additional 2 mL of 0.5$\underline{M}$ Na$_2$HPO$_4$ to maintain pH=6.5. The reaction mixture was stirred overnight at 0° C., quenched with 6$\underline{M}$ HCl, diluted with water, and extracted 3× with CH$_2$Cl$_2$. The combined organic layers were dried over Na$_2$SO$_4$ and concentrated on a rotary evaporator. The crude product was again dissolved in CH$_2$Cl$_2$ and made basic to pH=11 with 15% NaOH. The mixture was washed 3× with diethyl ether, reacidified to pH=2 with 6$\underline{M}$ HCl, extracted 3× with CH$_2$Cl$_2$, dried over Na$_2$SO$_4$ and concentrated on a rotary evaporator yielding the pure keto-acid-ester compound (0.198 g, 75%).

The keto-acid-ester (0.300 g, 1.25 mmol) was dissolved in 2.5 mL of methanol. To this solution 0.240 g (10 mmol, 8 equiv.) of lithium hydroxide and 0.280 g (5 mmol, 4 equiv.) of potassium hydroxide were added. The mixture stirred for 48 hrs and was acidified with 6$\underline{M}$ HCl to pH=2. The mixture was diluted with 2.5 mL water and extracted 3× with CH$_2$Cl$_2$. The combined organic layers were dried over Na$_2$SO$_4$ and concentrated on a rotary evaporator. The crude product was again dissolved in CH$_2$Cl$_2$ and made basic to pH=11 with 15% NaOH. The mixture was washed 3× with CH$_2$Cl$_2$, dried over Na$_2$SO$_4$ and concentrated on a rotary evaporator yielding the pure title compound (0.167 g, 63%).

EXAMPLE 3

2-[carboxy(hydroxy)methylidenyl]-5-[carboxy (hydroxy)methylidenyl]cyclopentanone (5)

Cyclopentanone (0.300 g, 3.57 mmol) was combined with 0.572 g (3.92 mmol, 1.1 equiv.) of diethyl oxalate and cooled to 0° C. In a separate flask, 0.440 g (3.92 mmol, 1.1 equiv.) of potassium t-butoxide was suspended in 7.2 mL dry THF and cooled to 0° C. The cyclopentanone/diethyl oxalate mixture was added dropwise over 1 hour via syringe pump to the stirring THF solution at 0° C. The reaction was allowed to stir overnight and then acidified with 6$\underline{M}$ HCl to pH=2. The solution was diluted with 3.5 mL of water and extracted 3× with CH$_2$Cl$_2$. The combined organic layers were dried over Na$_2$SO$_4$ and concentrated on a rotary evaporator. Flash chromatography on silica gel, eluting with n-hexane/ethyl acetate (3:1) gave 0.558 g (85%) of the keto-ester.

The above keto-ester (0.300 g, 1.62 mmol) was combined with 0.263 g (1.8 mmol, 1.1 equiv.) of diethyl oxalate and cooled to 0° C. In a separate flask, 0.436 g (3.6 mmol, 2.2 equiv.) of potassium t-butoxide was suspended in 7.5 mL dry THF and cooled to 0° C. The keto-ester/diethyl oxalate mixture was added dropwise over 1 hour via syringe pump to the stirring THF solution at 0° C. The reaction was allowed to stir overnight and then acidified with 6$\underline{M}$ HCl to pH=2. The solution was diluted with 3.5 mL of water and extracted 3× with CH$_2$Cl$_2$. The combined organic layers were dried over Na$_2$SO$_4$ and concentrated on a rotary evaporator. Flash chromatography on silica gel, eluting with n-hexane/ethyl acetate (1:1) gave 0.430 g (86%) of a mixture of mono- and di-ethyl esters (1:5).

The keto-ester (0.300 g, 1.12 mmol) was dissolved in 2.5 mL of methanol. To this solution 0.214 g (8.95 mmol, 8 equiv.) of lithium hydroxide and 0.251 g (4.47 mmol, 4 equiv.) of potassium hydroxide were added. The mixture stirred for 48 hrs and was acidified with 6$\underline{M}$ HCl to pH=2. The mixture was diluted with 2.5 mL water and extracted 3× with CH$_2$Cl$_2$. The combined organic layers were dried over Na$_2$SO$_4$ and concentrated on a rotary evaporator. The crude product was again dissolved in CH$_2$Cl$_2$ and made basic to pH=11 with 15% NaOH. The mixture was washed 3× with diethyl ether, reacidified to pH=2 with 6$\underline{M}$ HCl, extracted 3× with CH$_2$Cl$_2$, dried over Na$_2$SO$_4$ and concentrated on a rotary evaporator yielding the pure title compound (0.183 g, 72%). 300 MHz $^1$H NMR (CDCl$_3$) δ 16.39 (s, 2H), 2.18 (s, 4H). IR (neat) vmax 3284 (m), 2964 (m), 2855 (w), 1731 (s), 1702 (s), 1651 (s), 1634 (s), 1541 (s), 1339 (m), 1266 (m), 1185 (s), 1010 (m), 913 (w), 830 (m), 795 (s).

EXAMPLE 4

2-Hydroxy-4-oxo-2-octendioic acid (4)

4-acetylbutyric acid (0.300 g, 2.31 mmol) was combined with 0.371 g (2.54 mmol, 1.1 equiv.) of diethyl oxalate and cooled to 0° C. In a separate flask, 0.620 g (5.07 mmol, 2.2 equiv.) of potassium t-butoxide was suspended in 4.6 mL dry THF and cooled to 0° C. The 4-acetylbutyric acid/diethyl oxalate mixture was added dropwise over 1 hour via syringe pump to the stirring THF solution at 0° C. The reaction was allowed to stir overnight and then acidified with 6$\underline{M}$ HCl to pH=2. The solution was diluted with 3.5 mL of water and extracted 3× with CH$_2$Cl$_2$. The combined organic layers were dried over Na$_2$SO$_4$ and concentrated on a rotary evaporator. Flash chromatography on silica gel, eluting with n-hexane/ethyl acetate (3:1) gave 0.450 g (91%) of the keto-acid-ester.

The keto-acid-ester (0.300 g, 1.4 mmol) was dissolved in 2.5 mL of methanol. To this solution 0.134 g (5.6 mmol, 4 equiv.) of lithium hydroxide and 0.157 g (2.8 mmol, 2 equiv.) of potassium hydroxide were added. The mixture stirred for 48 hrs and was acidified with 6$\underline{M}$ HCl to pH=2. The mixture was diluted with 2.5 mL water and extracted 3× with CH$_2$Cl$_2$. The combined organic layers were dried over Na$_2$SO$_4$ and concentrated on a rotary evaporator. The crude product was again dissolved in CH$_2$Cl$_2$ and made basic to pH=11 with 15% NaOH. The mixture was washed 3× with diethyl ether, reacidified to pH=2 with 6$\underline{M}$ HCl, extracted 3× with CH$_2$Cl$_2$, dried over Na$_2$SO$_4$ and concentrated on a rotary evaporator yielding the pure title compound (0.269 g, 95%). 300 MHz $^1$H NMR (CDCl$_3$) δ 2.56–2.51 (t, 2H), 2.42–2.37 (t, 2H), 2.15 (s, 2H), 1.95–1.85 (m, 2H). IR (neat) vmax 3161 (s), 2940 (s), 2670 (s), 1734 (s), 1686 (s), 1653 (m), 1453 (s), 1418 (s), 1363 (s), 1285 (s), 1160 (s), 1069 (m), 947 (m), 840 (m), 742 (m), 667 (w).

EXAMPLE 5

2-[2'-carboxy(ethyl)]-6-[carboxy(hydroxy) methylidenyl]cyclohexanone (3)

To a stirred solution of 1-morpholino-1-cyclohexene (0.300 g, 1.8 mmol) in 5 mL dry dioxane was added 0.222 g (2.6 mmol, 1.44 equiv.) of methyl acrylate. After refluxing for 48 hours, the reaction mixture was quenched with 10 mL of water and refluxed for an additional 8 hours. The resulting mixture was cooled to room temperature and extracted with 1:1 diethyl ether/1$\underline{M}$ HCl. The combined organic layers were dried over Na$_2$SO$_4$ and concentrated on a rotary evaporator. Flash chromatography on silica gel, eluting with n-hexane/ethyl acetate (4:1) gave 0.323 g (87%) of the keto-ester as a colorless viscous liquid.

The above keto-ester (0.300 g, 1.63 mmol) was combined with 0.262 g (t.79 mmol, 1.1 equiv.) of diethyl oxalate and cooled to 0° C. In a separate flask, 0.274 g (2.45 mmol, 1.5 equiv.) of potassium t-butoxide was suspended in 3.5 mL dry THF and cooled to 0° C. The keto-ester/diethyl oxalate mixture was added dropwise over 1 hour via syringe pump to the stirring THF solution at 0° C. The reaction was allowed to stir overnight and then acidified with 6$\underline{M}$ HCl to pH=2. The solution was diluted with 3.5 mL of water and extracted 3× with $CH_2Cl_2$. The combined organic layers were dried over $Na_2SO_4$ and concentrated on a rotary evaporator. Flash chromatography on silica gel, eluting with n-hexane/ethyl acetate (4:1) gave 0.394 g (90%) of the bis-ethyl ester.

The bis-ethyl ester (0.300 g, 1.12 mmol) was dissolved in 2.5 mL of methanol. To this solution, 0.214 g (8.95 mmol, 8 equiv.) of lithium hydroxide and 0.251 g (4.48 mmol, 4 equiv.) of potassium hydroxide were added. The mixture stirred for 48 hrs and was acidified with 6$\underline{M}$ HCl to pH=2. The mixture was diluted with 2.5 mL water and extracted 3× with $CH_2Cl_2$. The combined organic layers were dried over $Na_2SO_4$ and concentrated on a rotary evaporator. The crude product was again dissolved in $CH_2Cl_2$ and made basic to pH=11 with 15% NaOH. The mixture was washed 3× with diethyl ether, reacidified to pH=2 with 6$\underline{M}$ HCl, extracted 3× with $CH_2Cl_2$, dried over $Na_2SO_4$ and concentrated on a rotary evaporator yielding the pure title compound (0.246 g, 97%) as a white solid. 300 MHz $^1H$ NMR ($CDCl_3$) δ 2.50–2.46 (m, 3H), 2.15–2.03 (m, 4H), 1.87–1.71 (m, 2H). IR (neat) vmax 3095 (ss), 2936 (s), 2863 (s), 1732 (s), 1699 (s), 1450 (s), 1419 (s), 1313 (s), 1227 (s), 1132 (m), 940 (w), 833 (w).

EXAMPLE 6

Soybean Cyst Nematode Egg Hatching Evaluation

The effects of representative compounds of the invention on the in vitro hatching time of SCN was evaluated following the general procedures disclosed by A. T. S. Wong et al., J. Nematology, 25, 578 (1993). Specifically, aqueous solutions of the compounds were prepared using deionized water previously adjusted to pH 7.0 with 1.0M HCl and 1.0M KOH. An Iowa population of SCN was cultured on Glycine max (L.) Merrill 'Corsoy 79' in the greenhouse. Immediately before experimentation, adult females and cysts were removed from 30-day-old soybean roots on a 850-µm-pore sieve with a high-pressure stream of water. The females and cysts were collected on a 250-µm pore sieve and subsequently separated from soil and root debris by sucrose centrifugation. (W. R. Jenkens, Plant Disease Reporter, 48, 692 (1964).) Females and cysts were crushed with a motorized pestle to release the eggs (H. R. Boerma et al., J. Nematology, 16, 289 (1984)). Females and cysts or eggs were surface disinfested with 0.5% chlorhexidine diacetate for 15 minutes and rinsed repeatedly with sterile water (J. R. Acedo et al., J. Nematology, 14, 418 (1982)).

Individual hatching units consisted of a microsieve, tray, and eggs. The microsieves were constructed from circles of nylon monofilament screen (38-µm pores) stretched over the end of an 18-mm-d cylinder and inserteel into a 20-mm-d cylinder; cylinders were polypropylene test-tube caps with the ends removed. The microsieves were placed into 32-mm-wide×72-mm-long×14-mm-deep rectangular polystyrene trays with grid patterns inscribed on the bottom to facilitate counting of second stage juveniles (J2) that hatch and pass through the pores in the microsieves.

At the beginning of each experiment, the trays and sieves were exposed to radiation from a 30 W germicidal UV light for at least 30 minutes. A minimum of 5,000 eggs were dispensed onto each microsieve, which was placed immediately into the tray containing 12 ml of the solutions of the test compounds or a control solution. Deionized water, adjusted to pH 7.0 with 1.0M HCl and 1.0M KOH, and 3.14 mM zinc sulfate a SCN egg hatching stimulant reported by A. J. Clarke et at., Ann. Appl. Biol., 58, 497 (1966), were negative and positive controls, respectively. The hatching units were placed in 20-cm-wide×27-cm-long×9.5-cm-deep polystyrene containers and were randomized within complete blocks (each container contained one replication of each treatment), with five replicas per treatment. The eggs were incubated in darkness at 25±2 C., except when the hatching units were removed and the microsieves were transferred to new trays. Every other day for 24 days, the microsieves and eggs were transferred to freshly sterilized trays filled with fresh solution, and the J2 remaining in the old trays were counted. At the end of each experiment, the number of unhatched eggs remaining on each microsieve was determined. The individual counts of J2 were converted into percentages of the total eggs.

The results of this study are summarized on Table 1, below.

TABLE 1

Hatching of free soybean cyst nematode eggs after 14 and 28 days of incubation in four synthetic glycinoeclepin A analogs relative to hatching in deionized water and 3.14 mM zinc sulfate solution.

| | | Percentage difference from: | | | |
| | | deionized water | | zinc sulfate | |
| Compound | Concentration (PPM) | Day 14 | Day 28 | Day 14 | Day 28 |
| --- | --- | --- | --- | --- | --- |
| 1 | 1 | +1.8 | +0.9 | −16.6 | −19.3 |
| 1 | 54 | −11.6 | −16.8 | −30.0 | −37.0 |
| 2 | 5 | −9.8 | −11.4 | −13.3 | −9.7 |
| 2 | 50 | −46.2 | −54.5 | −49.9 | −48.9 |
| 3 | 10 | −3.7 | −3.0 | −18.6 | −20.7 |
| 3 | 100 | −3.8 | −5.9 | −18.7 | −23.6 |
| 4 | 10 | −3.0 | −3.6 | −17.9 | −21.3 |
| 4 | 100 | −5.3 | −7.3 | −20.2 | −25.0 |

Data presented are means of 5 replications per treatment. Large negative differences from deionized water indicate inhibition of hatch; small negative or positive differences from zinc sulfate indicate stimulation of hatch.

As shown by the data on Table 1, compound 1 significantly inhibited the hatch of soybean cyst nematode eggs at Day 14 and 28. Percentage hatch in 54 parts per million of 1 was also significantly less than the hatch in deionized water after 14 and 28 days. Additional experiments with compound 1 revealed that the eggs were not killed, but were simply prevented from hatching by the material. Once eggs were removed from compound 1 and placed in deionized water or zinc sulfate, a more normal hatch of the eggs was observed. These results indicate that compound 1 is not lethal to the eggs and thus, may effectively and specifically prevent the nematode eggs from hatching while having no harmful nontarget effects on insects, livestock, or humans.

Compounds 2–5 also consistently inhibited hatching of SCN eggs at concentrations comparable to those which yielded significant inhibition with compound 1.

In addition to the laboratory hatching assays mentioned above, compounds 1 and 2 were tested in sterilized soils in several growth chamber experiments. Both compounds 1 and 2 inhibited hatching of SCN eggs in the sterilized soils, indicating that the compounds are not inactivated by chemical or physical conditions in soil environments. This result is critical because the compounds must be active in the soil to be of practical use in management of SCN in the field.

The results obtained with Compounds 1–4 were unexpected, since these compounds share structural features with glycinoecleptin A, a hatch stimulant. However, these compounds have great potential for use in management of soybean cyst nematodes. Compounds 1–4 inhibited soybean cyst nematode egg hatch at concentrations that would be feasible for application on a large scale field basis. Soybean roots are infected each spring by soybean cyst nematode juveniles that hatch from eggs. Damage to soybean plants and subsequent yield loss due to the nematode may be lessened or completely alleviated if nematode infection of the roots can be delayed by inhibition of egg hatching for a period of as little as a few weeks.

All publications are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for inhibiting hatching of soybean cyst nematode eggs comprising contacting said eggs with an effective inhibitory amount of a compound of formula (I):

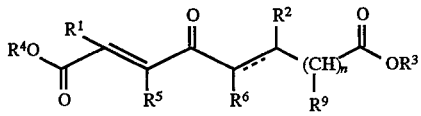

wherein $R^1$ is H or OH, $R^2$ is H or OH, $R^3$ is H or $(C_1-C_4)$alkyl, $R^4$ is H or $(C_1-C_4)$alkyl, $R^5$ and $R^6$ are individually H, $(C_1-C_5)$alkyl, $C_3-C_6$(cycloalkyl)alkyl, $C_5-C_7$(cycloalkenyl)alkyl, $(C_6-C_{12})$aryl, $(C_7-C_{12})$aralkyl, trans$(C_4-C_5)$alkenyl, allyl or furan-2-ylalkyl or together are $(C_2-C_5)$alkylene, or $(C_3-C_5)$alkylidene or 1,2-phenylene, optionally substituted by OH, $O(C_1-C_3)$alkyl, SH, phenyl or $N(R^7)(R^8)$, wherein $R^7$ and $R^8$ are individually H, $(C_1-C_3)$alkyl or phenyl; $R^9$=H or $(C_1-C_4)$alkyl, n is 0 or 1 and wherein the bond represented by --- is present when n=0 or absent when n=1; or an agronomically-acceptable salt thereof.

2. The method of claim 1 comprising applying to a plot of soil infested with said eggs with an amount of a compound of formula (I) effective to inhibit the hatching of said eggs, in combination with an agronomically-acceptable carrier.

3. The method of claim 1 wherein a solution or a dispersion of the compound of formula (I) in a liquid carrier is sprayed onto the soil.

4. The method of claim 2 wherein the carrier is a powdered solid.

5. The method of claim 4 wherein the amount of the compound of formula (I) is absorbed onto a powdered solid carrier that is then dispersed in a liquid vehicle.

6. The method of claim 1 wherein $R^2$ is OH, n=0 and the bond represented by --- is present.

7. The method of claim 1 wherein $R^2$ is H, n=1 and the bond represented by --- is absent.

8. The method of claim 1 wherein $R^3$ and $R^4$ are H.

9. The method of claim 1 wherein $R^5$ and $R^6$ together are ethylene, propylene or butylene.

10. The method of claim 9 wherein $R^1$ and $R^2$ are OH, n=0 and the bond represented by --- is present.

11. The method of claim 8 wherein $R^1$ is OH, $R^2$ is H and the bond represented by --- is absent.

12. The method of claim 1 wherein $R^5$ and $R^6$ are H.

13. The method of claim 12 wherein $R^1$ is OH, n=1, $R^2$ is H and the bond represented by --- is absent.

14. The method of claim 1 wherein the compound of formula (I) is 2-(2'-carboxyethyl)-5-(carboxymethylidenyl)cyclopentanone.

15. The method of claim 1 wherein the compound of formula (I) is 2-(2'-carboxyethyl)-5-[carboxy(hydroxy)methylidenyl]cyclopentanone.

16. The method of claim 1 wherein the compound of formula (I) is 2-(2'-carboxyethyl)-6-[carboxy(hydroxy)methylidenyl]cyclohexanone.

17. The method of claim 1 wherein the compound of formula (I) is 2-[carboxy(hydroxy)methylidenyl]-5-[carboxy(hydroxy)methylidenyl]cyclopentanone.

18. The method of claim 1 wherein the compound of formula (I) is 2-hydroxy-4-oxo-2-octendioic acid.

* * * * *